(12) United States Patent
Hayner

(10) Patent No.: US 10,207,719 B2
(45) Date of Patent: Feb. 19, 2019

(54) USE OF MULTIPLE INTERNAL SENSORS FOR MEASUREMENTS VALIDATION

(75) Inventor: David A. Hayner, Austin, TX (US)

(73) Assignee: NXP USA, Inc., Austin, TX (US)

(*) Notice: Subject to any disclaimer, the term of this patent is extended or adjusted under 35 U.S.C. 154(b) by 1210 days.

(21) Appl. No.: 12/838,633

(22) Filed: Jul. 19, 2010

(65) Prior Publication Data
US 2012/0016623 A1    Jan. 19, 2012

(51) Int. Cl.
| | |
|---|---|
| G01C 19/00 | (2013.01) |
| G01C 25/00 | (2006.01) |
| G01D 18/00 | (2006.01) |
| G01F 19/00 | (2006.01) |
| B60W 50/02 | (2012.01) |
| G01N 27/416 | (2006.01) |
| B60W 50/00 | (2006.01) |

(52) U.S. Cl.
CPC ......... B60W 50/0205 (2013.01); G01D 18/00 (2013.01); G01N 27/4163 (2013.01); *B60W 2050/0031* (2013.01); *B60W 2420/90* (2013.01); *B60W 2520/105* (2013.01); *B60W 2520/125* (2013.01); *B60W 2520/14* (2013.01)

(58) Field of Classification Search
CPC .. G01N 27/4163; G01D 18/00; G01D 18/008; B60W 2520/105; B60W 2420/90
USPC .................................................. 702/104, 116
See application file for complete search history.

(56) References Cited

U.S. PATENT DOCUMENTS

| | | | | |
|---|---|---|---|---|
| 4,868,771 | A | * | 9/1989 | Quick et al. ....................... 703/8 |
| 5,291,607 | A | | 3/1994 | Ristic et al. |
| 5,774,378 | A | * | 6/1998 | Yang .............................. 702/104 |
| 5,875,257 | A | * | 2/1999 | Marrin et al. ................. 382/107 |
| 6,161,905 | A | * | 12/2000 | Hac et al. ....................... 303/146 |
| 6,182,001 | B1 | * | 1/2001 | Sugai et al. ..................... 701/78 |
| 6,366,833 | B1 | * | 4/2002 | Fukuyama ....................... 701/1 |
| 6,725,168 | B2 | * | 4/2004 | Shiraishi et al. ............... 702/81 |
| 7,236,091 | B2 | | 6/2007 | Kiang et al. |
| 7,245,215 | B2 | | 7/2007 | Gollu et al. |

(Continued)

FOREIGN PATENT DOCUMENTS

| | | |
|---|---|---|
| JP | 2002-362121 | * 12/2002 |
| WO | WO 2006/128916 | * 12/2006 |
| WO | WO 2007/045787 | *  4/2007 |

OTHER PUBLICATIONS

Definition of Inertia, Online Dictionary, printed Jan. 30, 2013.*

(Continued)

*Primary Examiner* — Michael P Nghiem (57) ABSTRACT

A microcontroller-based method and apparatus are described for measuring motions signals (301) with a plurality of inertial sensors (302-304) contained within a device package housing and validating (420) a first measured motion signal (e.g., $\Omega_X$) by generating at least a first estimated value $\Omega_X$ for the first motion signal (e.g., 419) based on at least a second measured motion signal (e.g., $A_Y$) and for comparing the first estimated value for the first motion signal (419) to the first measured motion signal $\Omega_X$ in order to validate the first measured motion signal $\Omega_X$.

16 Claims, 4 Drawing Sheets

(56) References Cited

U.S. PATENT DOCUMENTS

| | | | |
|---|---|---|---|
| 7,376,499 B2* | 5/2008 | Salman | G01R 31/2829 340/425.5 |
| 7,434,464 B2 | 10/2008 | Li | |
| 7,792,620 B2* | 9/2010 | Fritz et al. | 701/42 |
| 2003/0055549 A1* | 3/2003 | Barta | B60G 17/0182 701/70 |
| 2003/0236604 A1* | 12/2003 | Lu et al. | 701/45 |
| 2004/0204910 A1* | 10/2004 | Brumbach et al. | 702/185 |
| 2006/0065050 A1* | 3/2006 | Saito et al. | 73/511 |
| 2007/0067085 A1* | 3/2007 | Lu et al. | 701/70 |
| 2007/0260383 A1* | 11/2007 | Sundaram et al. | 701/70 |
| 2008/0270162 A1* | 10/2008 | Machacek | 705/1 |
| 2008/0290430 A1 | 11/2008 | Mahadevan et al. | |
| 2009/0031809 A1 | 2/2009 | Lin et al. | |
| 2009/0043405 A1* | 2/2009 | Chester et al. | 700/28 |
| 2009/0299579 A1* | 12/2009 | Hac | B60G 17/0162 701/46 |
| 2009/0299695 A1* | 12/2009 | Subbu et al. | 702/181 |
| 2009/0326851 A1* | 12/2009 | Tanenhaus | 702/96 |

OTHER PUBLICATIONS

English Abstract of CN 201405839, Feb. 17, 2010.*
Wikipedia, The Free Encyclopedia, Mathematical model, http://en.wikipedia.org/wiki/Dynamic_model (accessed Nov. 16, 2012).
R. Becker, Introduction to Theoretical Mechanics, (1954), 9 pages.

* cited by examiner

USE OF MULTIPLE INTERNAL SENSORS FOR MEASUREMENTS VALIDATION

BACKGROUND OF THE INVENTION

Field of the Invention

The present invention is directed in general to the field of inertial sensor measurements systems. In one aspect, the present invention relates to a system and methodology for validating measurements from inertial sensor devices.

Description of the Related Art

Micro-Electro-Mechanical Systems (MEMS) technology is increasingly used to integrate mechanical elements, sensors, actuators, and electronics onto very small mechanical structures which can be used to take inertial measurements. For example, inertial sensors may be formed with MEMS devices on an integrated circuit wafer substrate to form various applications, such as a MEMS gyroscope that is used to detect the rate of change of a position variable (e.g., angular position) for an object, or a MEMS linear accelerometer that is used to measure the rate of increase or decrease in the velocity of an object. To ensure that a specific inertial measurement or sequence of measurements has not been corrupted or detected in error, conventional systems will attempt to validate an inertial measurement by using redundant sensors and/or correlations with alternative external measurements. For example, an inertial measurement of a vehicle's movement from a MEMS accelerometer sensor (e.g., vehicle linear acceleration in a given vehicle axis) is compared against or validated with different measures or references of the vehicle's movement (e.g., wheel speed, wheel angle, etc.) which are obtained with separate sensors which are external to the MEMS gyroscope sensor. However, errors and delays can be introduced when assembling and comparing measurement data from different sensors positioned around a vehicle.

Accordingly, a need exists for an improved sensor measurement apparatus, system and method of operations that addresses various problems in the art that have been discovered by the above-named inventor where various limitations and disadvantages of conventional solutions and technologies will become apparent to one of skill in the art after reviewing the remainder of the present application with reference to the drawings and detailed description which follow, though it should be understood that this description of the related art section is not intended to serve as an admission that the described subject matter is prior art.

BRIEF DESCRIPTION OF THE DRAWINGS

The present invention may be understood, and its numerous objects, features and advantages obtained, when the following detailed description is considered in conjunction with the following drawings, in which.

DETAILED DESCRIPTION

A packaged multi-sensor device and associated methodology are described for taking a plurality of sensor measurements from sensors within the packaged multi-sensor device, and then using the measurements to cross-validate at least one of the sensor measurements. The sensors can be inertial sensors, such as accelerometers or gyros, motion sensors, mechanical sensors, pressure sensors, temperature sensors, magnetic stress sensors, magnetic field sensors, optical sensors, chemical sensors, or any arbitrary type of sensor. In selected embodiments, the packaged multi-sensor device is implemented with analog circuitry, digital circuitry or a combination thereof, and includes one or more gyro sensors and one or more linear accelerometer sensors, and also includes a processing system which uses dynamic models of a vehicle system to predict one or more inertial measures in one domain from actual measured signals in another domain so that the predicted inertial measure(s) can be compared against an actual measured signal for purposes of validation. By leveraging multiple sensor measurements from within the packaged multi-sensor device and applying knowledge of the dynamics of the vehicle platform, a first predicted inertial effect (e.g., linear acceleration in the z-direction) can be computed from one or more measured inertial effects (e.g., roll angular velocity, y-axis acceleration, etc.), and then compared to an actual measurement of the first inertial effect (e.g., actual sensed z-axis acceleration) for validating the actual measurement and/or providing an estimate or quantification of the validity of this measure. Thus, the packaged multi-sensor device can not only measure a plurality of various inertial effects (and possibly other inputs), but can also assess the accuracy or validity of these measures without the need for external measures, thereby reducing the cost and improving the reliability of a multi-sensor system that can be used in a variety of applications, such as automotive, industrial and aerospace products. A packaged multi-sensor device and associated methodology of operation are described for dynamically measuring and validating one or more inertial effects by using a plurality of internal sensors contained within a packaged sensor device to measure one or more inertial effects, and using a digital processing system (e.g., processing unit or microcontroller) that is also contained within the packaged device to compute predicted values from selected inertial signal measurements for purposes of validating one or more inertial signal measurements. In selected embodiments, a packaged multi-sensor device is implemented with a plurality of inertial sensors (e.g., a gyro transducer element with one or more linear accelerometer sensors), an analog/digital interface circuit and a micro-controller unit (MCU) which are assembled together on a common package. In single package architecture, each of the plurality of inertial sensors contains the physical mechanical devices which together sense inertial measures (e.g., angular velocity, acceleration, etc). The interface circuit serves as an analog/digital interface between the sensors and the MCU, such as by converting changes in capacitance to voltages, performing analog signal conditioning, providing A/D and D/A conversion, and providing an analog gain control loop and frequency sourcing. The MCU calculates predicted values from selected inertial signal measurements, and in various ways, compares or correlates the predicted and measured values to quantify the validity of the signal measurements and improve the quality or accuracy of the measurements and aid in the detection of potential failed or failing sensors.

Various illustrative embodiments of the present invention will now be described in detail with reference to the accompanying figures which illustrate functional and/or logical block components and various processing steps. It should be appreciated that such block components may be realized by any number of hardware, software, and/or firmware components configured to perform the specified functions. For the sake of brevity, conventional techniques related to semiconductor processing, MEMS processing, and sensor technology are not described herein. While various details are set forth in the following description, it will be appreciated that the present invention may be practiced without these specific details, and that numerous implementation-specific decisions may be made to the invention described herein to achieve the device designer's specific goals, such as compliance with process technology or design-related constraints, which will vary from one implementation to another. While such a development effort might be complex and time-consuming, it would nevertheless be a routine undertaking for those of ordinary skill in the art having the benefit of this disclosure. For example, selected embodiments of the present invention are implemented, for the most part, with electronic components and circuits known to those skilled in the art, and as a result, circuit details have not been explained in any greater extent since such details are well known and not considered necessary to teach one skilled in the art of how to make or use the present invention. In addition, selected aspects are depicted with reference to simplified signal model, hardware flow chart drawings without including every circuit detail or feature in order to avoid limiting or obscuring the present invention. Such descriptions and representations are used by those skilled in the art to describe and convey the substance of their work to others skilled in the art.

Figure 1:
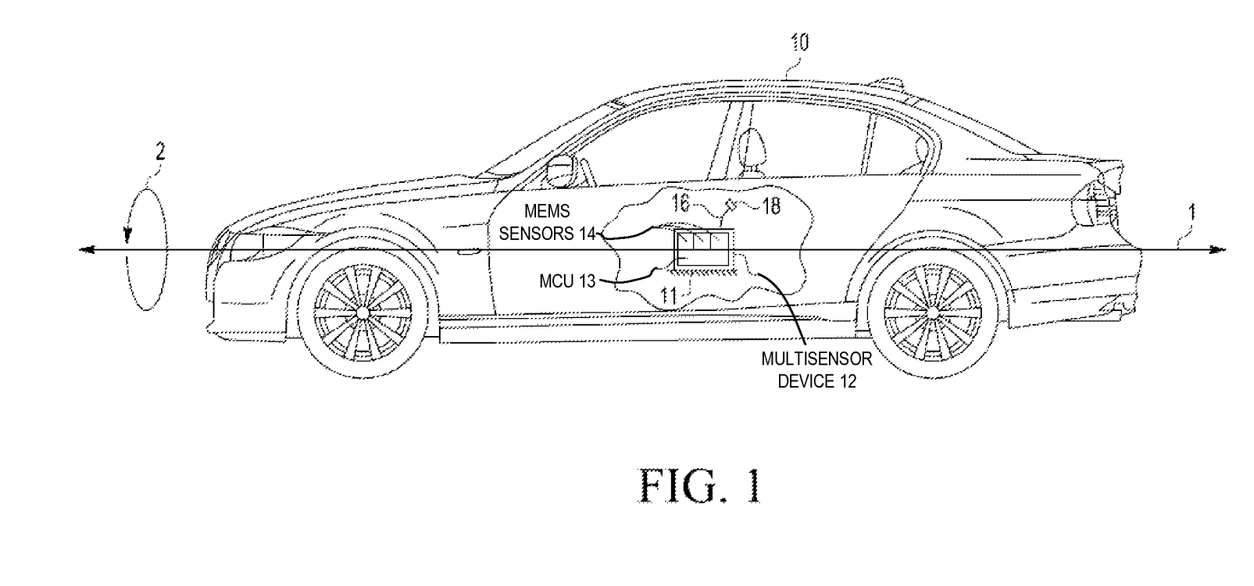
FIG. 1 depicts a vehicle about which inertial effects are measured using MEMS sensor devices to sense the inertial effects.

FIG. 1 depicts an object 10 about which inertial effects are measured using MEMS sensor devices which transform physical inertial effects into electrical measurement signals. Object 10 is depicted in the form of a vehicle platform with sensors mounted in the vehicle (e.g., at the center of gravity) to measure physical effects to control the deployment of airbags, to assist in stability management, and the like. For example, the measured physical effects may include acceleration along the axis of acceleration 1 and/or the angular rotation rate around the axis of rotation 2. However, it will be appreciated that other types of platforms may also serve as the object 10, including but not limited to trains, planes, trucks. In addition, other apparatuses may be used, such as cameras which include sensors for measuring physical effects for image stabilization purposes; hard disk drives and laptops which include sensors for measuring physical effects for free-fall detection; game controllers, cell phones, and/or personal digital assistants (PDAs) which include sensors for measuring physical effects for gesture recognition and/or tilt sensing; and other types of apparatuses which benefit from transducing physical effects into electrical signals.

The depicted vehicle object 10 includes a base support structure 11 positioned in both location and orientation to experience and/or benefit from the physical effects of interest. As shown, the base support structure 11 may be located centrally, but the base support structure 11 may be located elsewhere, such as in the passenger compartment or elsewhere. Mounted to the base support structure 11 is a multi-sensor device 12 which includes an MCU processing unit 13 and a plurality of micro-electrical-mechanical systems (MEMS) sensors 14. The sensors 14 may be formed on an integrated circuit wafer substrate, and may include any type of inertial or other sensor. Each of the sensors 14 generates and/or responds to electrical signals 16 provided over a wired, optical, or RF link 18 in a manner well understood to those of skill in the art, thereby enabling communication with other devices or circuits (e.g., airbags) located elsewhere in the vehicle object 10. In an example implementation, the multi-sensor device 12 may be constructed as a small and inexpensive package which encloses the MCU 13 and processors 14, thereby allowing other packaged multi-sensor devices (not shown) to be included in a given volume of space which would heretofore have been impractical.

Figure 2:
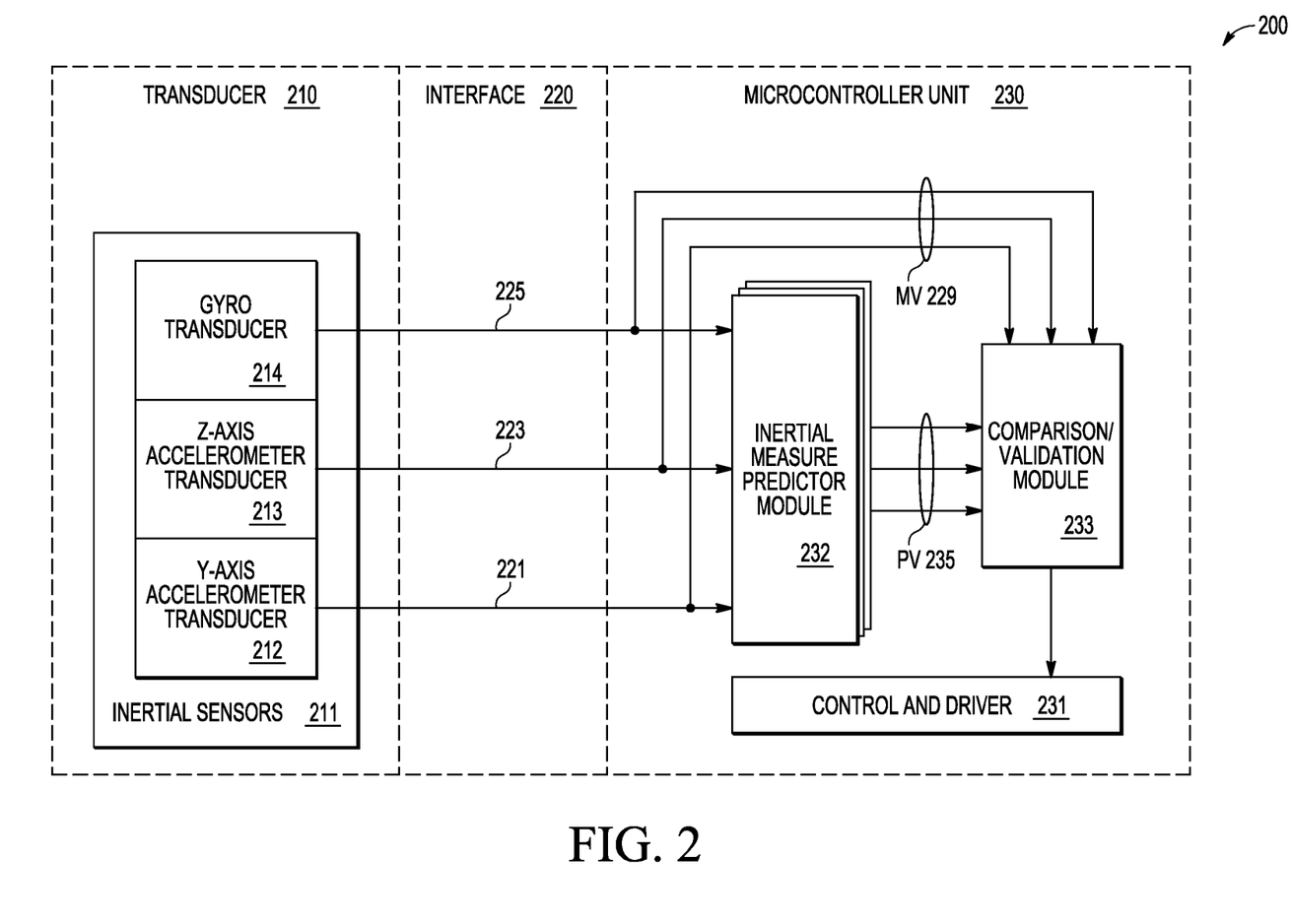
FIG. 2 is a block diagram view of a MEMS inertial sensor system which uses multiple internal sensors to measure and validate detected inertial effects.

FIG. 2 is a block diagram view of a MEMS inertial sensor system 200 which uses multiple internal sensors 211 to measure and validate detected inertial effects. As depicted, the MEMS inertial sensor system 200 includes a transducer section 210, an interface circuit section 220 and a processing unit or micro-controller unit (MCU) section 230, all of which may be contained within a common package housing device (indicated with dashed lines) which encapsulates the transducer, interface circuit, and MCU sections with a molding compound. For example, the transducer, interface circuit, and MCU sections may be implemented with one or more die which are attached to one or more lead frame die flags, wirebonded to provide interior electrical connections, and the over-molded or transfer molded with a composite material (e.g., plastic) to create a molded device package housing.

The transducer section 210 of the MEMS inertial sensor system 200 includes a plurality of inertial sensors 211 that are selected according to the requirements of a given MEMS inertial sensor application. In selected applications where a vehicle is placed in the x-y plane when x, y, and z are orthogonal axes defining a three dimensional space, the transducer section 210 includes a plurality or cluster of inertial sensors (including but not limited to one or more accelerometers and/or gyroscopes) that are positioned to measure linear acceleration and/or roll angular velocity values in or around the three-dimensional axis directions. In the depicted application, the sensors 211 include a y-axis accelerometer transducer 212, a z-axis accelerometer transducer 213, and one or more gyroscope transducers 214, all of which may be formed on one or more integrated circuit wafer substrates. Though not explicitly shown, it will be appreciated that the interface circuit section 220 includes conversion circuitry for interfacing the analog transducer circuitry 210 with the digital MCU circuitry 230, including but not limited to signal conditioning circuitry for receiving and converting measurement signals 221, 223, 225 generated respectively by the transducers 212, 213, 214 into digital measured signal values MV 229.

In the depicted example of FIG. 2, the MCU section 230 includes control and driver circuitry 231, a prediction module 232, and a comparison or validation module 233. As used herein, a module can be software or hardware that is implemented with separate circuitry and/or as a process operation of a processor core or other processor circuitry. Thus, the prediction module 232 is processing or hardware functionality for receiving the measured signal values MV 229 (which have been converted to digital form), and calculating therefrom one or more predicted signal values PV 235. At the comparison or validation module 233, the predicted signal values PV 235 are adjudicated by comparing predetermined predicted signal values PV 235 with the corresponding actual measured signal values 229 that originated from the transducers 211. In addition, the MCU section 230 includes control and driver circuitry 231 which may be used to activate a separate function or circuit upon detection and validation of an inertial effect meeting one or more predetermined activation criteria. For example, if a measured linear acceleration signal value exceeds a threshold activation value (e.g., from a sudden deceleration), the control and driver circuitry 231 may be used to control the deployment of airbags, to assist in stability management, and the like.

As will be appreciated, the MCU section 230 may include a central processing unit (CPU), CPU control circuit, arithmetic logic unit (ALU), internal control registers, pointers, and program counters. Such a configuration provides a microprocessor core with the ability to control, monitor, and change control based on instructions and signals. The MCU section 230 receives and/or processes control signals, and provides the control signals and data to the control and driver circuitry/section 231. Though not shown, additional circuits are included in the MCU section 230, such as power output drivers, static random access memory (SRAM), read only memory (ROM), and timers. In addition to being implemented with one or more microprocessor cores, the MCU section 230 can be implemented with other data processing circuits for processing and validating data signals generated by the sensors 211 and producing one or more outputs which control from the control and driver section 231, such as microcontroller circuits, reduced instruction set computer (RISC) circuits, fuzzy logic circuits, neural networks, and the like. Generally speaking, the MCU section 230 may be implemented with a small amount of memory and logic devices which are dedicated to performing elementary logical operations for processing and validating the measured signal values MV 229. All of these means for data processing differ primarily in scale of processing capability rather than fundamental principle of operation for the MCU section 230.

In an example operation of the MEMS inertial sensor system 200, the inertial sensors 212-214 generate inertial measures of the y-axis linear acceleration (y_accel) and the roll angular velocity ($\Omega_x$), respectively. Once converted into digital measured signal values MV 229 by the interface circuit section 220, these are applied to both the prediction module 232 and the validation module 233. At the prediction module 232, an estimated or predicted signal value for the z-axis linear acceleration (z_âccel) is computed from the measured y-axis linear acceleration (y_accel) and roll angular velocity ($\Omega_x$) values. The predicted z-axis linear acceleration (z_âccel) signal value is then compared at the validation module 233 to the actual inertial measure of the z-axis linear acceleration (z_accel) generated by the z-axis transducer 213, thereby validating the actual measurement signal for the z-axis linear acceleration (z_accel). In this example, the inertial measures of the y-axis linear acceleration (e.g., "y") and the roll angular velocity (e.g., "x") are used to generate an estimated or predicted signal value for the z-axis linear acceleration (e.g., "z") such that z=F(x,y), but it will be appreciated that the predicted z value can also be generated from the x value alone (e.g., z=F(x)), from the y value alone (or z=F(y)), from a combination of x and z (e.g., z=F(x,z)), from a combination of y and z (e.g., z=F(y,z)), and/or from a combination of x, y, and z (e.g., z=F(x,y,z)). Thus, with three original measures, six different estimates of a given signal "z" can be generated. The same is true for generating multiple estimates of the roll angular velocity (e.g., "x"), including F1(y), F2(z), F3(x,y), F4(x,z), F5(y,z), and/or F6(x,y,z). Likewise, multiple estimates of the y-axis linear acceleration (e.g., "y"), including F1(x), F2(z), F3(x,y), F4(x,z), F5(y,z), and/or F6(x,y,z). In this way, multiple measures can be combined in a wide variety of ways to obtain different estimates of any one of the signals.

As will be appreciated, a variety of techniques may be used to compute estimated signal values from one or more measured signal values. In selected embodiments, one set of vehicle dynamics may be estimated from measured vehicle signals using a state-space model which provides a matrix version of a set of Nth order linear differential equations representing the dynamics of the specific vehicle (model type) on which the sensor(s) are mounted. To provide an example state space model, reference is made to the following equations $\dot{x}$=Ax+Bu and y=Cx+Du, where A is an N×N matrix, B is an N×M matrix, C is a K×N matrix, and D is a K×M matrix, the state vector x is an N×1 matrix, the output vector X is an N×1 matrix representing the derivative dx(t)/dt of the state vector x, the input vector u is an M×1 matrix, and the output vector y is a K×1 matrix. To further illustrate this example, the matrix equations may be represented as:

$$\begin{bmatrix} \dot{x}_1 \\ \dot{x}_2 \\ \dot{x}_3 \\ \dot{x}_4 \end{bmatrix} = \begin{bmatrix} a_{11} & a_{12} & a_{13} & a_{14} \\ a_{21} & a_{22} & a_{23} & a_{24} \\ a_{31} & a_{32} & a_{33} & a_{34} \\ a_{41} & a_{42} & a_{43} & a_{44} \end{bmatrix} \begin{bmatrix} x_1 \\ x_2 \\ x_3 \\ x_4 \end{bmatrix} + \begin{bmatrix} b_{11} & b_{12} \\ b_{21} & b_{22} \\ b_{31} & b_{32} \\ b_{41} & b_{42} \end{bmatrix} \begin{bmatrix} u_1 \\ u_2 \end{bmatrix} \text{ and}$$

$$\begin{bmatrix} y_1 \\ y_2 \\ y_3 \end{bmatrix} = \begin{bmatrix} c_{11} & c_{12} & c_{13} & c_{14} \\ c_{21} & c_{22} & c_{23} & c_{24} \\ c_{31} & c_{32} & c_{33} & c_{34} \end{bmatrix} \begin{bmatrix} x_1 \\ x_2 \\ x_3 \\ x_4 \end{bmatrix} + \begin{bmatrix} d_{11} & d_{12} \\ d_{21} & d_{22} \\ d_{31} & d_{32} \end{bmatrix} \begin{bmatrix} u_1 \\ u_2 \end{bmatrix}$$

In this case, the input may be vehicle roll and/or yaw and/or x acceleration and the output may be updated estimates of the input signals. For example, u1 could represent vehicle yaw and u2 could represent vehicle x acceleration for inputs. The outputs y1, y2 and y3 could be vehicle pitch, vehicle roll, and vehicle y acceleration. Of course, the inputs (u1 and u2) and outputs (y1, y2, and y3) could represent other sensor values. With this example, the A, B, C, and D matrix values are a function of the specific vehicle (model) and the specific measured inputs and desired estimated outputs. Of course, the methods used to generate the A, B, C, and D matrix values are varied, including but not limited to system design/analysis techniques, system identification methods, Kalman filtering concepts, etc. In the case above, the matrix elements can be time varying, or may be functions of other system parameters (e.g., temperature, vehicle speed, tire inflation, etc.). While this specific mathematical form does not directly address the use of non-linear models, similar methods of using analytical models of system input-output relationships can be used to reliably estimate one set of system dynamics from another set of system measurements. In addition, it is noted that these methods are often used to effectively filter a system measure.

Figure 3:
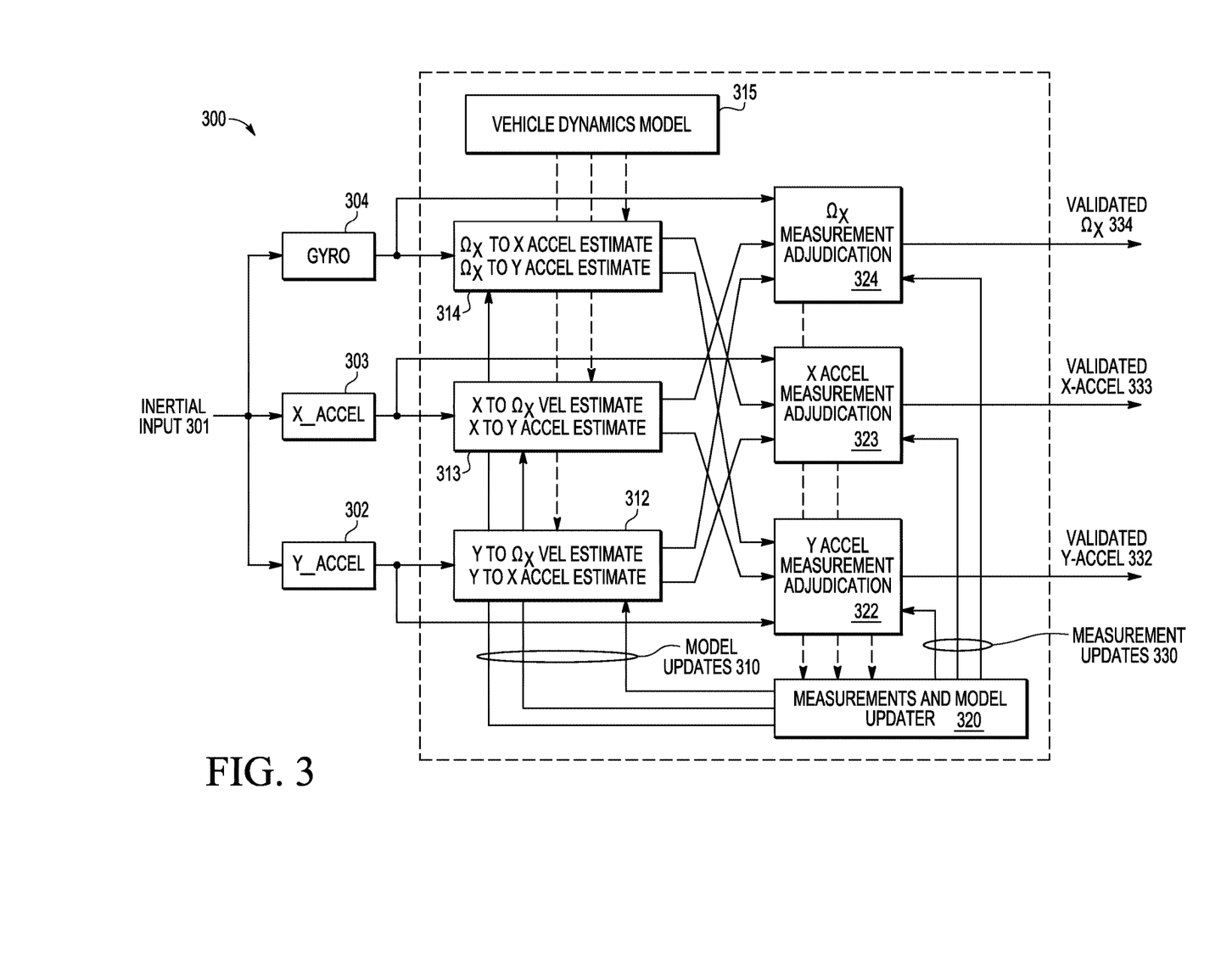
FIG. 3 is a simplified block diagram of the digital processing system functionality for receiving and validating a plurality of inertial sensor measurements.

To further illustrate selected embodiments of the present invention, reference is now made to FIG. 3 which depicts a simplified block diagram of the digital processing system functionality 300 for receiving and validating a plurality of inertial sensor measurements. Generally speaking, the sensors 302-304 shown in FIG. 3 correspond to the internal sensors 211 shown in FIG. 2, the estimation units 312-314 shown in FIG. 3 correspond to the prediction module 232 shown in FIG. 2, and the adjudication units 322-324 shown in FIG. 3 correspond to the comparison or validation module 233 shown in FIG. 2. As depicted, an inertial input condition 301 relating to the movement of a platform is detected by a plurality of internal inertial sensors 302-304 which may be contained within a common package. For example, the inertial input condition 301 may be converted into a plurality of measured inertial signals by one or more gyro sensors 304 and one or more linear accelerometers 302-303. The measured inertial signals are then processed by the MCU processing section 300 which may be implemented with digital and/or analog circuitry. By applying dynamic models of the sensors 302-304 and the platform carrying the sensors (e.g., a vehicle) that are retrieved from a vehicle dynamics model 315, the MCU processing section 300 calculates one or more predicted inertial signal values from the actually measured inertial signal values. In the depicted example, the roll angular velocity processing unit 314 uses the measured roll angular velocity signal ($\Omega_X$) to estimate the x-axis and y-axis linear acceleration values, and these estimated x-axis and y-axis linear acceleration values are applied, respectively, to the x-axis acceleration measurement adjudication unit 323 and the y-axis acceleration adjudication unit 322. Likewise, the x-axis accelerator processing unit 313 uses the measured x-axis linear acceleration signal (x_accel) to estimate the roll angular velocity signal ($\Omega_X$) and y-axis linear acceleration values, which are in turn are applied, respectively, to the roll angular velocity measurement adjudication unit 324 and the y-axis acceleration adjudication unit 322. Finally, the y-axis accelerator processing unit 312 uses the measured y-axis linear acceleration signal (y_accel) to estimate the roll angular velocity signal ($\Omega_X$) and x-axis linear acceleration values, which are in turn are applied, respectively, to the roll angular velocity measurement adjudication unit 324 and the x-axis acceleration adjudication unit 323.

By applying the actual measured inertial signals and the corresponding predicted or estimated inertial signals to the associated measurement adjudication unit, the predicted inertial signals can be used to validate the actual measured inertial signal and otherwise provide a quantification of the validity of the signal measurement. For example, the roll angular velocity measurement adjudication unit 324 receives the actual measured inertial signal value for the roll angular velocity from the gyro sensor(s) 304, and also receives estimated signal values of the roll angular velocity from the y-axis accelerator processing unit 312 and the x-axis accelerator processing unit 313. In this way, one or more of the predicted measures of the roll angular velocity can be used to validate the actual measurement of the roll angular velocity and generate a validated output signal 334. In addition, the validated output signal 334 may also include an estimate of the validity of this measure. In similar fashion, the x-axis acceleration measurement adjudication unit 323 receives and processes the actual and estimated inertial signal values for the x-axis acceleration to generate a validated output signal 333, and the y-axis acceleration measurement adjudication unit 322 receives and processes the actual and estimated inertial signal values for the y-axis acceleration to generate a validated output signal 332.

Figure 4:
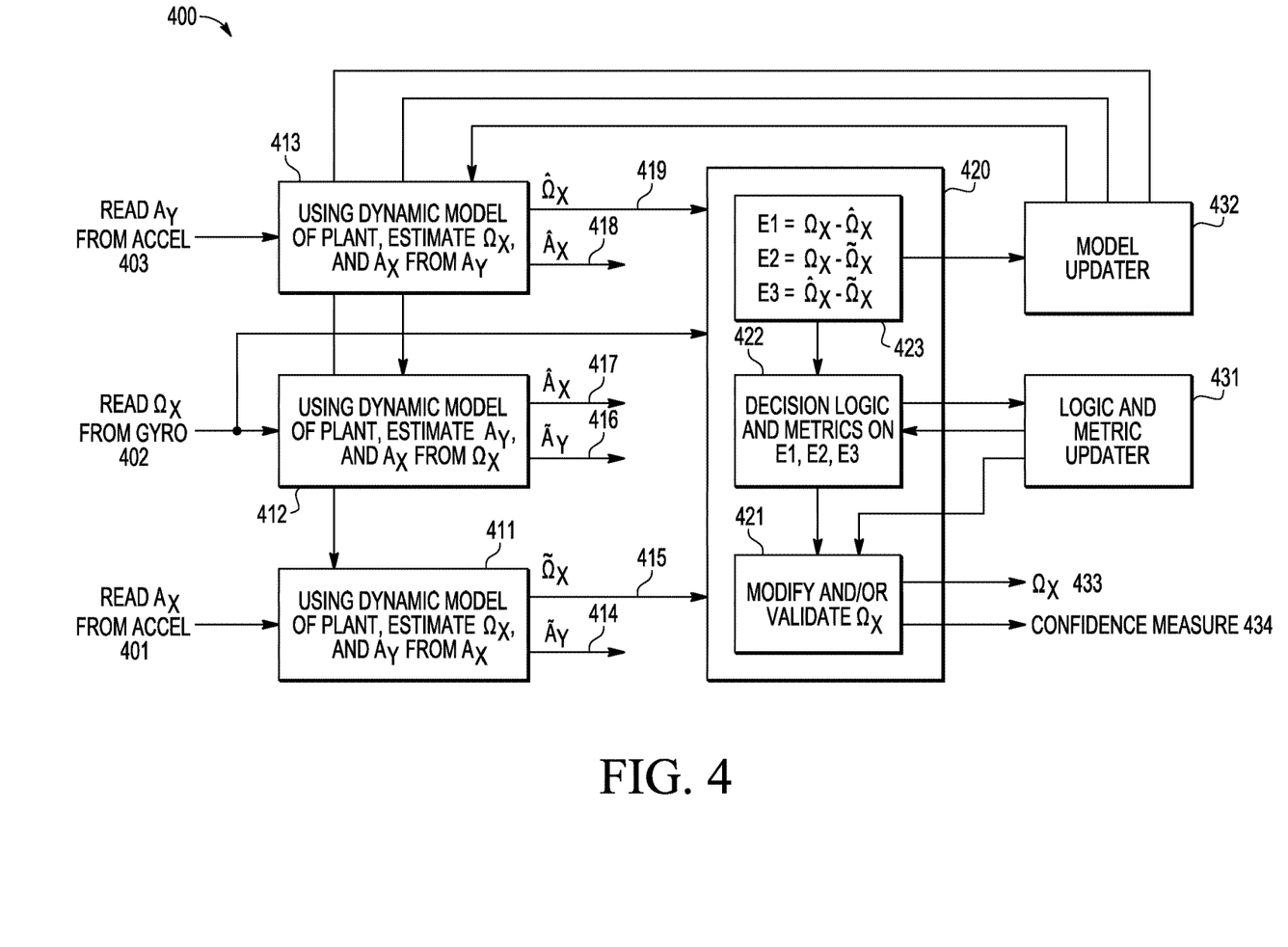
FIG. 4 depicts a signal processing flow chart for validating measured inertial signals by using dynamic models to predict values for the inertial signals based on measurements of other inertial signals.

FIG. 4 depicts a signal processing flow chart 400 for validating measured inertial signals in accordance with selected embodiments by using dynamic models to predict values for the inertial signals based on measurements of other inertial signals. Generally speaking, the steps 411-413, 420 shown in FIG. 4 are performed by the prediction module 232 and comparison or validation module 233 shown in FIG. 2. The process begins at steps 401-403 when inertial signal value measurements are read from the inertial sensors. In this example, the measured x-axis acceleration signal value Ax is read at step 401, the measured roll angular velocity signal value $\Omega_X$ is read at step 402, and the measured y-axis acceleration signal value Ay is read at step 403. In selected embodiments, the inertial sensor readings may be filtered (e.g., with a Kalman filter) or otherwise processed to improve the signal quality.

At step 413, the measured y-axis acceleration signal value $A_Y$ is used to compute values for the estimated x-axis acceleration signal value $A_X$ 418 and the roll angular velocity value $\Omega_X$ 419. This computation at step 413 is performed by applying knowledge of the dynamics of the platform and/or sensors which are dynamically provided by the model updater 432. In addition or in the alternative, the measured roll angular velocity signal value $\Omega_X$ is processed at step 412 to compute estimated values for the y-axis acceleration signal value $A_Y$ 416 and the x-axis acceleration signal value $A_X$ 417 by applying knowledge of the dynamics of the platform and/or sensors which are dynamically provided by the model updater 432. Finally, the measured x-axis acceleration signal value $A_X$ may also be processed at step 411 to compute estimated values for the y-axis acceleration signal value $A_Y$ 414 and the roll angular velocity value $\Omega_X$ 415 by applying knowledge of the dynamics of the platform and/or sensors which are dynamically provided by the model updater 432.

At step 420, the measured roll angular velocity value $\Omega_X$—which is read from the gyro at step 402—is validated by comparison to one or more estimated values for the roll angular velocity value $\Omega_X$ 415, 419. The validation process can be a straightforward comparison algorithm for making sure the estimated and measured values corroborate one another. For example, one or more error measurement values may be calculated at step 423 based on the estimated and measured values of the roll angular velocity value $\Omega_X$. In a first error measurement value E1, the estimated roll angular velocity value $\Omega_X$ 419 computed at step 413 is subtracted from the measured roll angular velocity value $\Omega_X$. In addition or in the alternative, a second error measurement value E2 is computed by subtracting the estimated roll angular velocity value $\Omega_X$ 415 computed at step 411 from the measured roll angular velocity value $\Omega_X$. Another error measurement value E3 may be computed by subtracting the estimated roll angular velocity value $\Omega_X$ 419 computed at step 413 from the estimated roll angular velocity value $\Omega_X$ 415 computed at step 411. As will be appreciated, more sophisticated comparison techniques can be used to evaluate a measured roll angular velocity value against one or more estimates of the roll angular velocity value that are derived from other measured values. For example, a first error value E1 may be generated using statistical and/or time weighted techniques for comparison with the first estimated roll angular velocity signal value.

At step 422, decision logic and associated metrics are retrieved form the logic and metric updater 431 and applied to the one or more computed error measurements E1, E2, E3. The results from step 422 are processed at the modification/validation step 421 for purposes of validating the measured roll angular velocity value $\Omega_X$ or otherwise modifying the measured roll angular velocity value $\Omega_X$. For example, the results of the modification/validation step 421 may be to output a validated roll angular velocity value $\Omega_X$ 433 along with an associated confidence measure 434 to provide an estimate of the validity of this measure.

As described herein, the validation step 420 of a measured roll angular velocity value $\Omega_X$ is described with reference to an example sequence whereby error estimates E1-E3 are generated based on measured and estimated values of the roll angular velocity value $\Omega_X$, decision logic and metrics are applied to the error estimates E1-E3 to determine validity and/or confidence in the measured roll angular velocity value $\Omega_X$ data and generate a confident. In addition or in the alternative, these steps can be repeated to validate the measured y-axis acceleration signal value $A_Y$ and/or the measured z-axis acceleration signal value $A_Z$. For example, the measured y-axis acceleration signal value $A_Y$ can be validated at step 420 by comparing the measured y-axis acceleration signal value $A_Y$ to one or more estimated values for the y-axis acceleration signal value $A_Y$ that are computed or estimated from the measured z-axis acceleration signal value $A_Z$ and the measured roll angular velocity value $\Omega_X$, respectively, such as by computing and subtracting error values E1-E3. By applying decision logic and metrics with weighting factors to the error estimates E1-E3 for the y-axis acceleration signal value $A_Y$, the measured y-axis acceleration signal value $A_Y$ can be modified and/or validated, and a confidence measure can be determined. Likewise, the measured z-axis acceleration signal value $A_Z$ can be validated at step 420 by comparing the measured z-axis acceleration signal value $A_Z$ to one or more estimated values for the z-axis acceleration signal value $A_Z$ that are computed or estimated from the measured y-axis acceleration signal value $A_Y$ and the measured roll angular velocity value $\Omega_X$, respectively, such as by computing and subtracting error values E1-E3. By applying decision logic and metrics with weighting factors to the error estimates E1-E3 for the z-axis acceleration signal value $A_Z$, the measured z-axis acceleration signal value $A_Z$ can be modified and/or validated, and a confidence measure can be determined. Again, it will be appreciated that more sophisticated decision methods can be used to validate a measured value.

By now, it should be appreciated that there has been disclosed a packaged multi-sensor device for measuring and validating one or more inertial effects and an associated method of operation. The disclosed multi-sensor device includes a device package housing which contains a plurality of sensors, such as inertial sensors for measuring or transducing signals, such as motion signals. In selected embodiments, the sensors are implemented as a gyroscope sensor, a first accelerometer sensor, and a second accelerometer sensor (e.g., MEMS gyroscope and accelerometer), and in other embodiments, the sensors include two or more sensors selected from a group comprising a gyroscope sensor, an accelerometer sensor, a motion sensor, a mechanical sensor, a pressure sensor, a temperature sensor, a magnetic stress sensor, a magnetic field sensor, an optical sensor, and a chemical sensor, all formed on a common integrated circuit substrate. The device package housing also contains a microcontroller for generating a first estimated value for a first motion signal based on at least a second measured motion signal, and for comparing the first estimated value for the first motion signal to the first measured motion signal in order to validate the first measured motion signal. An application specific integrated circuit or other interface circuit is coupled as an analog/digital interface between the inertial sensors and the microcontroller. With this configuration, the microcontroller may be configured to compute the first estimated value for the first motion signal (e.g., the estimated z-axis linear acceleration value and/or the estimated y-axis linear acceleration value) based on the second measured motion signal (e.g., the measured roll angular velocity value $\Omega_X$) and the platform dynamics modeling information for a platform on which the packaged multi-sensor device is mounted. Once the estimated values are computed, the microcontroller validates the first measured motion signal (e.g., the measured z-axis linear acceleration value transduced by a first inertial sensor) by comparing the measured z-axis linear acceleration value to an estimated z-axis linear acceleration value which is derived from at least a second inertial sensor. And as described herein, the microcontroller may be configured to validate another measured signal value transduced by a first inertial sensor by comparing the measured signal value to an estimated signal value which is derived from at least another inertial sensor. In general terms, the microcontroller validates a first measured signal x that is transduced by a first inertial sensor by comparing the measured signal x to an estimated signal x' which is derived from a second measured signal y; from a third measured signal z; from a combination of the second measured signal y and the third measured signal z; from a combination of the measured signal x and the second measured signal y; from a combination of the measured signal x and the third measured signal z; or from a combination of the measured signal x, the second measured signal y, and the third measured signal z. In this arrangement, the microcontroller validates a first measured signal x that is transduced by a first sensor by comparing the measured signal x to one or more estimated signals x' where each of the one or more estimated signals x' is derived from at least one or more additional measured signals y transduced from one or more additional sensors.

In another form, there is provided a method, system, and integrated circuit package for validating one or more measured inertial values associated with a platform without using external reference information. In the disclosed methodology, measurements are taken of a plurality of inertial values in a plurality of domains, including at least a first measured inertial value in a first domain and a second measured inertial value in a second different domain. The measurements may be taken by reading a y-axis acceleration signal value Ay from a first linear accelerometer sensor, reading a z-axis acceleration signal value Az from a second linear accelerometer sensor, and reading a roll angular velocity signal value $\Omega_X$ from one or more gyro sensors. A first estimated inertial value in the first domain is calculated using at least the second measured inertial value in the second different domain. For example, the first estimated inertial value may be calculated by applying a dynamic model of the platform to calculate a first estimated roll angular velocity signal value $\Omega_{X1}$ using the y-axis acceleration signal value Ay, and to calculate a second estimated roll angular velocity signal value $\Omega_{X2}$ using the z-axis acceleration signal value Az. Finally, the first estimated inertial value is compared to the first measured inertial value to assess a validity measure for the first measured inertial value. In an example embodiment, the comparison may be implemented by generating a first error value E1 by subtracting the first estimated roll angular velocity signal value $\Omega_{X1}$ from the roll angular velocity signal value $\Omega_X$, generating a second error value E2 by subtracting the second estimated roll angular velocity signal value $\Omega_{X2}$ from the roll angular velocity signal value $\Omega_X$, and generating a third error value E3 by subtracting the second estimated roll angular velocity signal value $\Omega_2$ from the first estimated roll angular velocity signal value $\Omega_{X1}$. In other embodiments, the comparison of the first estimated inertial value to the first measured inertial value comprises generating a first error value E1 using statistical and/or time weighted techniques for comparison with the first estimated inertial signal value. In addition, decision logic may be applied to the error values E1, E2, E3 to assess the validity measure for the roll angular velocity signal value $\Omega_X$. In another example, the estimated inertial value may be calculated by applying a dynamic model of the platform to calculate a first estimated y-axis acceleration signal value $A_{Y1}$ using the roll angular velocity signal value $\Omega_X$, and to calculate a second estimated y-axis acceleration signal value $A_{Y2}$ using the z-axis acceleration signal value Az. In this example, the comparison of the first estimated inertial value to the first measured inertial value may be implemented by generating a first error value E1 by subtracting the first estimated y-axis acceleration signal value $A_{Y1}$ from the y-axis acceleration signal value Ay, generating a second error value E2 by subtracting the second estimated y-axis acceleration signal value $A_{Y2}$ from the y-axis acceleration signal value $A_Y$, and generating a third error value E3 by subtracting the second estimated y-axis acceleration signal value $A_{Y2}$ from the first estimated y-axis acceleration signal value $A_{Y1}$. By applying decision logic to these error values E1, E2, E3, the validity measure for the y-axis acceleration signal value $A_Y$ may be assessed.

In yet another form, there is provided a method, system, and integrated circuit package for using a plurality of inertial sensors in a packaged multi-sensor device to measure and validate one or more inertial measurements. In the disclosed system and methodology, a plurality of inertial values in a plurality of domains are read or sensed using the plurality of inertial sensors in a packaged multi-sensor device to obtain at least a first measured inertial value in a first domain and one or more additional measured inertial value in one or more different domains. A dynamic model of the packaged multi-sensor device and a platform carrying the packaged multi-sensor device is applied to calculate a first estimated inertial value in the first domain using at least the one or more additional measured inertial values in the one or more different domains. The computed first estimated inertial value is compared to the first measured inertial value to assess a validity measure for the first measured inertial value, such as by generating one or more error values by calculating one or more first estimated inertial values in the first domain using at least the one or more additional measured inertial values in one or more different domains and subtracting the one or more first estimated inertial values from the first measured inertial value to assess the validity measure for the first measured inertial value.

Although the exemplary embodiments disclosed herein are directed to validating signals that are measured using MEMS sensor structures in a single packaged sensor device without using external measures or references, the present invention is not necessarily limited to the example embodiments, but is applicable to a wide variety of packaged sensor devices, manufacturing methods and operational methodologies. For example, while the MEMS sensors are described as a combination of gyroscope and linear accelerator sensors, any of a number of different MEMS sensor devices may be used to generate the measured inertial signals, including but not limited to motion sensors, mechanical sensors, pressure sensors, temperature sensors, magnetic stress sensors, magnetic field sensors, optical sensors, and chemical sensors. In addition, the process steps may be performed in an alternative order than what is presented. Thus, the particular embodiments disclosed above are illustrative only and should not be taken as limitations upon the present invention, as the invention may be modified and practiced in different but equivalent manners apparent to those skilled in the art having the benefit of the teachings herein. As a result, the foregoing description is not intended to limit the invention to the particular form set forth, but on the contrary, is intended to cover such alternatives, modifications and equivalents as may be included within the spirit and scope of the invention as defined by the appended claims so that those skilled in the art should understand that they can make various changes, substitutions and alterations without departing from the spirit and scope of the invention in its broadest form.

Benefits, other advantages, and solutions to problems have been described above with regard to specific embodiments. However, the benefits, advantages, solutions to problems, and any element(s) that may cause any benefit, advantage, or solution to occur or become more pronounced are not to be construed as a critical, required, or essential feature or element of any or all the claims. The term "coupled," as used herein, is not intended to be limited to a direct coupling or a mechanical coupling. As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

What is claimed is:

1. A packaged multi-sensor device for measuring and validating one or more inertial signals, comprising:
a plurality of sensors arranged to measure at least first, second, and third inertial signals in different domains, the plurality of sensors comprising a first Micro-Electro-Mechanical Systems (MEMS) sensor device for measuring the first inertial signal in a first domain, a second MEMS sensor device for measuring the second inertial signal in a second different domain, and a third MEMS sensor device for measuring the third inertial signal in a third different domain; and
a processing unit for generating first and second estimated values for the first inertial signal based on, respectively, the second and third inertial signals, and for comparing the first and second estimated values for the first inertial signal to the first inertial signal in order to validate the first inertial signal,
where the processing unit generates the first estimated value by computing a first estimated x-axis linear acceleration value from the second inertial signal which comprises a measured roll angular velocity value $\Omega_X$, and
where the processing unit generates the second estimated value by computing a second estimated x-axis linear acceleration value from the third inertial signal which comprises a measured y-axis linear acceleration value.

2. The packaged multi-sensor device of claim 1, where the plurality of sensors comprises a Micro-Electro-Mechanical Systems (MEMS) gyroscope sensor and an MEMS accelerometer sensor.

3. The packaged multi-sensor device of claim 1, where the plurality of sensors comprises two or more sensors selected from a group comprising a gyroscope sensor, an accelerometer sensor, a motion sensor, a mechanical sensor, a pressure sensor, a temperature sensor, a magnetic stress sensor, a magnetic field sensor, an optical sensor, and a chemical sensor, all formed on a common integrated circuit substrate.

4. The packaged multi-sensor device of claim 1, further comprising an interface integrated circuit coupled between the plurality of sensors and the processing unit which serves as an analog/digital interface between the plurality of sensors and the processing unit.

5. The packaged multi-sensor device of claim 1, where the processing unit validates the first inertial signal, which comprises a first measured x-axis linear acceleration value in a first direction that is transduced by the first MEMS sensor device, by comparing the first measured x-axis linear acceleration value to the first and second estimated x-axis linear acceleration values in the first direction which are derived, respectively, from the second and third MEMS sensor devices.

6. The packaged multi-sensor device of claim 1, where the processing unit validates a first measured signal x that is transduced by the first MEMS sensor device by comparing the first measured signal x to a first estimated signal x' which is derived from a second measured signal y; from a third measured signal z; from a combination of the second measured signal y and the third measured signal z; from a combination of the measured signal x and the second measured signal y; from a combination of the measured signal x and the third measured signal z; or from a combination of the measured signal x, the second measured signal y, and the third measured signal z.

7. The packaged multi-sensor device of claim 1, where the processing unit validates a first measured signal x that is transduced by a first sensor by comparing the measured signal x to a plurality of estimated signals x' where each of the estimated signals x' is derived from at least one or more additional measured signals y transduced from one or more additional sensors.

8. The packaged multi-sensor device of claim 1, where the processing unit is configured to generate the first estimated value for the first inertial signal based on the second inertial signal and platform dynamics modeling information for a platform on which the packaged multi-sensor device is mounted.

9. A packaged multi-sensor device for measuring and validating one or more inertial signals, comprising:
  a plurality of sensors arranged to measure at least first, second, and third inertial signals in different domains, the plurality of sensors comprising a first Micro-Electro-Mechanical Systems (MEMS) sensor device for measuring the first inertial signal in a first domain, a second MEMS sensor device for measuring the second inertial signal in a second different domain, and a third MEMS sensor device for measuring the third inertial signal in a third different domain; and
  a processing unit for generating first and second estimated values for the first inertial signal based on, respectively, the second and third inertial signals, and for comparing the first and second estimated values for the first inertial signal to the first inertial signal in order to validate the first inertial signal,
  where the processing unit generates the first estimated value by computing a first estimated y-axis linear acceleration value from the second inertial signal which comprises a measured roll angular velocity value $\Omega_X$, and
  where the processing unit generates the second estimated value by computing a second estimated y-axis linear acceleration value from the third inertial signal which comprises a measured x-axis linear acceleration value.

10. A packaged multi-sensor device for measuring and validating one or more inertial signals, comprising:
  a plurality of sensors arranged to measure at least first, second, and third inertial signals in different domains, the plurality of sensors comprising a first Micro-Electro-Mechanical Systems (MEMS) sensor device for measuring the first inertial signal in a first domain, a second MEMS sensor device for measuring the second inertial signal in a second different domain, and a third MEMS sensor device for measuring the third inertial signal in a third different domain; and
  a processing unit for generating first and second estimated values for the first inertial signal based on, respectively, at least the second and third inertial signals, and for comparing the first and second estimated values for the first inertial signal to the first inertial signal in order to validate the first inertial signal, where the processing unit validates the first inertial signal, which comprises a first measured linear acceleration value in a first direction that is transduced by the first MEMS sensor device, by comparing the first measured linear acceleration value to the first and second estimated values which are derived, respectively, from the second and third MEMS sensor device.

11. The packaged multi-sensor device of claim 10, where the processing unit generates the first estimated value by computing a first estimated x-axis linear acceleration value from the second inertial signal which comprises a measured roll angular velocity value $\Omega_X$ and where the processing unit generates the second estimated value by computing a second estimated x-axis linear acceleration value from the third inertial signal which comprises a measured y-axis linear acceleration value.

12. The packaged multi-sensor device of claim 10, where the processing unit generates the first estimated value by computing a first estimated y-axis linear acceleration value from the second inertial signal which comprises a measured roll angular velocity value $\Omega_X$ and where the processing unit generates the second estimated value by computing a second estimated y-axis linear acceleration value from the third inertial signal which comprises a measured x-axis linear acceleration value.

13. A packaged multi-sensor device for measuring and validating one or more inertial signals, comprising:
  a plurality of sensors arranged to measure at least first, second, and third inertial signals in different domains, the plurality of sensors comprising a first Micro-Electro-Mechanical Systems (MEMS) sensor device for measuring the first inertial signal in a first domain, a second MEMS sensor device for measuring the second inertial signal in a second different domain, and a third MEMS sensor device for measuring the third inertial signal in a third different domain; and
  a processing unit for generating first and second estimated values for the first inertial signal based on, respectively, the second and third inertial signals, and for comparing the first and second estimated values for the first inertial signal to the first inertial signal in order to validate the first inertial signal, where the processing unit validates the first inertial signal, which comprises a measured roll angular velocity value $\Omega_X$ that is transduced by first MEMS sensor device, by comparing the measured roll angular velocity value $\Omega_X$ to the first estimated value comprising a first estimated roll angular velocity value $\Omega_{X1}$ which is derived from the second MEMS sensor device and to the second estimated value comprising a second estimated roll angular velocity value $\Omega_{X2}$ which is derived from the third MEMS sensor device.

14. The packaged multi-sensor device of claim 13, where the processing unit generates the first estimated value by computing the first estimated roll angular velocity value $\Omega_{X1}$ from the second inertial signal which comprises a measured x-axis linear acceleration value and where the processing unit generates the second estimated value by computing the second estimated roll angular velocity value $\Omega_{X2}$ from the third inertial signal which comprises a measured y-axis linear acceleration value.

15. A packaged multi-sensor device for measuring and validating one or more inertial signals, comprising:
  a plurality of sensors arranged to measure at least first, second, and third inertial signals in different domains, the plurality of sensors comprising a first Micro-Electro-Mechanical Systems (MEMS) sensor device for measuring the first inertial signal in a first domain, a second MEMS sensor device for measuring the second inertial signal in a second different domain, and a third MEMS sensor device for measuring the third inertial signal in a third different domain; and
  a processing unit for generating first and second estimated values for the first inertial signal based on, respectively, at least the second and third inertial signals, and for comparing the first and second estimated values for the first inertial signal to the first inertial signal in order to validate the first inertial signal, where the processing unit generates the first and second estimated values by computing a first estimated roll angular velocity value $\Omega_{X1}$ from the second inertial signal which comprises a measured x-axis linear acceleration value and computing a second estimated roll angular velocity value $\Omega_{X2}$ from the third inertial signal which comprises a measured y-axis linear acceleration value.

16. The packaged multi-sensor device of claim 15, where the processing unit validates the first inertial signal, which comprises a measured roll angular velocity value $\Omega_X$ that is transduced by the first MEMS sensor device, by comparing the measured roll angular velocity value $\Omega_X$ to the first estimated roll angular velocity value $\Omega_{X1}$ which is derived from the second MEMS sensor device and to the second estimated roll angular velocity value $\Omega_{X2}$ which is derived from the third MEMS sensor device.

* * * * *